United States Patent [19]

Davidov

[11] Patent Number: 4,808,166

[45] Date of Patent: Feb. 28, 1989

[54] ANAL MEDICATION APPLICATOR

[76] Inventor: James Davidov, 21901 Burbank Blvd. #216, Woodland Hills, Calif. 91367

[21] Appl. No.: 105,897

[22] Filed: Oct. 8, 1987

[51] Int. Cl.$^4$ ............................................ A61M 29/00
[52] U.S. Cl. ...................................... 604/114; 604/60; 604/57; 128/303.12; 128/401
[58] Field of Search .................... 604/57, 59, 60, 113, 604/114, 61–64; 128/303.12, 401

[56] References Cited

U.S. PATENT DOCUMENTS

| | | | |
|---|---|---|---|
| 1,605,894 | 11/1926 | Homan | 604/114 |
| 4,122,850 | 10/1978 | Bucalo | 604/114 |
| 4,341,211 | 7/1982 | Kline | 604/60 |

*Primary Examiner*—Albert W. Davis, Jr.

[57] ABSTRACT

The anal medication applicator includes a long narrow hollow tubular container with an open front end, smooth closed sides and a generally central space connected to the open end, in which space the anal medication, solid or liquid is disposed. A plunger is disposed behind the medication in the space and extends rearwardly out of the container, for ejecting the medication gradually or suddenly out the front of the container. The plunger may be spring biased with a catch to releasably hold the plunger in the rear position. Upon release of the catch, the plunger will fire forward, suddenly ejecting the medication. A first set of electrical resistance wiring connected to a rheostat is disposed in the container around the central space to heat the medication. A second set of electrical resistance wiring controlled by a second rheostat can be utilized, separated from the first set by a thermal barrier in the container and disposed adjacent the outer surface of the container for heating the container before insertion into the anus. The applicator thus can provide selective heating of the container and/or medication for maximum utility and comfort. The applicator can be used in the treatment of hemorrhoids and for the prevention of Aquired Immune Deficiency Syndrome (AIDS).

6 Claims, 1 Drawing Sheet

ANAL MEDICATION APPLICATOR

BACKGROUND OF THE INVENTION

1. Field of the Invention

The present invention generally relates to medical apparatus and, more particularly, to an anal medication applicator of an improved type which has particular application to the treatment of hemorrhoids and prevention of anally transmittable diseases, such as Acquired Immune Deficiency Syndrome (AIDS)

PRIOR ART

The usual type of anal medication applicator is a plastic tube with a central passageway and side ports connected thereto. The applicator is screwed onto a flexible tube of anal medication which is then squeezed into the central passageway after the tube is inserted in the anus. The medication exits the tube through the open front and the side ports. Neither the tube nor the medication is heated and in fact may be cold to the touch, rendering insertion into the anus difficult and/or uncomfortable.

PRIOR ART STATEMENT

A search of the prior art has been made and various improved types of medication applicators as discussed below have been located and are described below. Thus, U.S. Pat. No. 453,508 is directed to a spring-loaded gun designed to fire a veterinary medication into a horse. U.S. Pat. No. 1,677,642 is directed to a medicinal applicator particularly for delivering a liquid to the arethra. The applicator comprises an electrically powered heating tube in tandem with an urethral tube connected to a syringe. The syringe holds the liquid medication until the applicator is in place, whereupon it is forced from the syringe and out through the urethral tube. While tissues may be heated by the heating tube, the liquid medication is not and can provide a cold shock to the area.

U.S. Pat. No. 3,032,036 discloses the use of an applicator for hemorrhoids, which applicator and medication are unheated. The medication is a treated fabric strip which has been chilled just before insertion, providing a shock to a tender anus. U.S. Pat. No. 2,078,686 discloses a complicated and expensive thermal dilator and medicator which consists of an externally fluted tube which may be disposed in an inflatable rubber balloon or sock. A source of electricity as well as compressed air is needed. Medication is first deposited on the exterior of the sock in the flute grooves. Internal heating may be provided in the tube to heat the tube and perhaps to some extent the medication and sock. Dilation of the sock after it is in place in the body cavity causes the medication to wipe off onto the body cavity. However, insertion of the fluted tube would be painful for anal treatment as would dilation of the sock. Delivery of medication by such means would be inefficient, the medication wiping off long before full rectal penetration.

Accordingly, there remains a need for an improved, inexpensive, efficient and durable anal medication applicator which provides improved ease and comfort of insertion and delivery of the medication to the rectum, as well as improved temperature control for the medication and applicator for therapeutic relief.

SUMMARY OF THE INVENTION

The improved anal medication applicator of the present invention satisfies all the foregoing needs. The applicator is substantially as set forth in the Abstract. Thus, the application comprises a long smooth hollow tubular container with a narrow diameter, an open rounded front end, closed smooth sides and central space communicating with the front end. The space contains a medication to be ejected from the front of the container by a preferably spring biased plunger or the like connected to the container, protruding into the space behind the medication and releasably hold by a catch. Thus, the medication can either be delivered by a manually pushed plunger or fired into the anus by a spring-actuated plunger.

The applicator includes means such as electrical resistance wiring for heating the medication in the space before delivery from the container while in the anus. Preferably, the wiring is disposed around the central space in the container and is connected to a rheostat on the container and an outside source of electrical power. The applicator may also include a second set of electrical resistance wiring or the like heating means, also preferably connected to a second separate rheostat and a power source and positioned adjacent the outer surface of the container in order to heat it. Preferably, the first and second heating means are separated in the container by a thermal barrier in the container so that the medication and/or container surfaces can be individually heated for optimal therapeutic effect.

The device is simple, compact, inexpensive and efficient. It can be inserted easily and painlessly, while heated and deliver a full dose of heated medication quickly and accurately. It may include graduated markings on the container and/or plunger to facilitate controlling the length of penetration of the container and/or medication.

Further features of the applicator are set forth in the following detailed description and accompanying drawings.

DRAWINGS

DETAILED DESCRIPTION

FIG. 1

Figure 1:
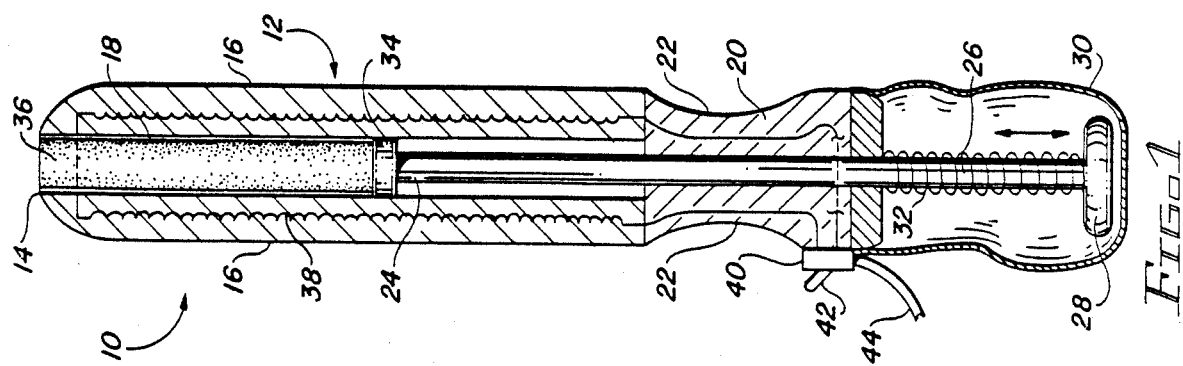
FIG. 1 is a schematic front elevation, partly broken away and partly in section, of a first preferred embodiment of the improved anal medication applicator of the present invention.

Now referring more particularly to FIG. 1 of the drawings, a first preferred embodiment of the improved anal medication applicator of the present invention is schematically depicted therein. Thus, applicator 10 is shown which comprises an elongated narrow diameter tubular container 12 having a rounded open front end 14 for ease of insertion in an anus and having smooth sides 16 without holes therein.

An elongated central space 18 is disposed the length of container 12 and communicates with open front end 14. The rear portion 20 of container 12 has curved side finger grips 22 and receives the elongated narrow shaft 24 of a plunger 26 having a rear handle 28 encased in a flexible resilient rubber or plastic sheath 30 connected to portion 20 for improved appearance. A return spring 32 may be connected to portion 20 and to shaft 24 to bias plunger 26 into the retracted position shown in FIG. 1.

The head 34 of plunger shaft 24 abuts the rear end of a plug 36 of solid anal medication disposed in space 18 so that plug 36 can be shoved out of front end 14 by plunger 26 after container 12 is inserted into the rectum, or, if desired, when placed near but outside the anal passage.

Before such ejection of plug 36, it is warmed by electrical resistance wiring 38 disposed around space 18 in container 12 and connected to a rheostat 40 having a temperature control lever 42 mounted on portion 20 of container 12. Rheostat 40 is connected to an electrical power source (house current or the like, not shown) by wiring 44. Wiring 38 may heat the outer surfaces of sides 16, if desired, as well as plug 36.

In any event, plug 36 may be initially inserted as a solid into space 18 from end 14, then heated therein before or while container 12 is in the anus and then delivered from container 12 into the anus as a warmed solid or a liquid, depending on the type of medication used, for maximum effectiveness. Warming of sides 16 by wiring 38 helps to make insertion of container 12 into the anus painless and easy and to provide the healing influence of warmth to that region of the body.

Applicator 10 is compact, simple, inexpensive, durable and efficient. Container 12 can be of metal, plastic, rubber, ceramic and/or other suitable materials and rheostat 40, wiring 38 and 44 and other components can be of conventional materials and design.

FIG. 2

Figure 2:
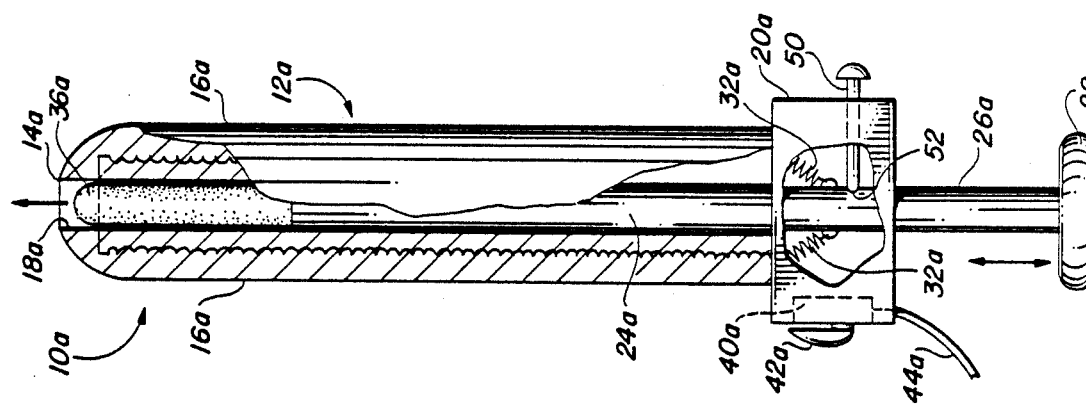
FIG. 2, is a schematic front elevation, partly broken away and partly in section, of a second preferred embodiment of the improved anal medication applicator of the present invention.

A second preferred embodiment of the improved anal medication applicator of the present invention is schematically depicted in FIG. 2. Thus, applicator 10a is shown. Components thereof similar to those of FIG. 1 bear the same numerals, but are succeeded by the letter "a".

Applicator 10a is substantially identical to applicator 10 except as follows:
(a) plug 36a is a hardened bullet-shaped solid loosely disposed in space 18a;
(b) plunger 26a has shaft 24a thereof connected to
  i. springs 32a which bias plunger 26a forwardly not rearwardly, and
  ii. to a catch in the form of a moveable side pin 50 extending through the side of portion 20a and into a catch hole or detent 52 in the side of shaft 24a. Pin 50 releasably holds shaft 24a in the rear retracted position shown in FIG. 2. Sliding pin 50 out of catch hole 52 causes plunger 26a to fire forward, driving medication bullet 36a out front 18a with force, far up into the rectum.
(c) no sheath such as 28 is disposed around handle 28a.

As in FIG. 1, wiring 38a heats bullet 36a before the described firing, with the temperature controlled by rheostat 40a through lever 42a and wiring 44a connected to a power source (not shown). Applicator 10a has the other advantages of applicator 10.

Figure 4:
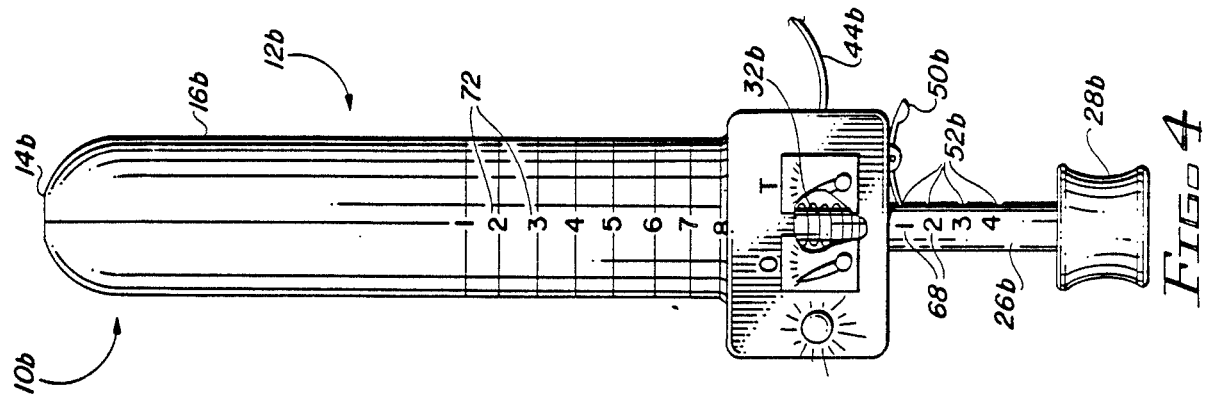
Figure 3:
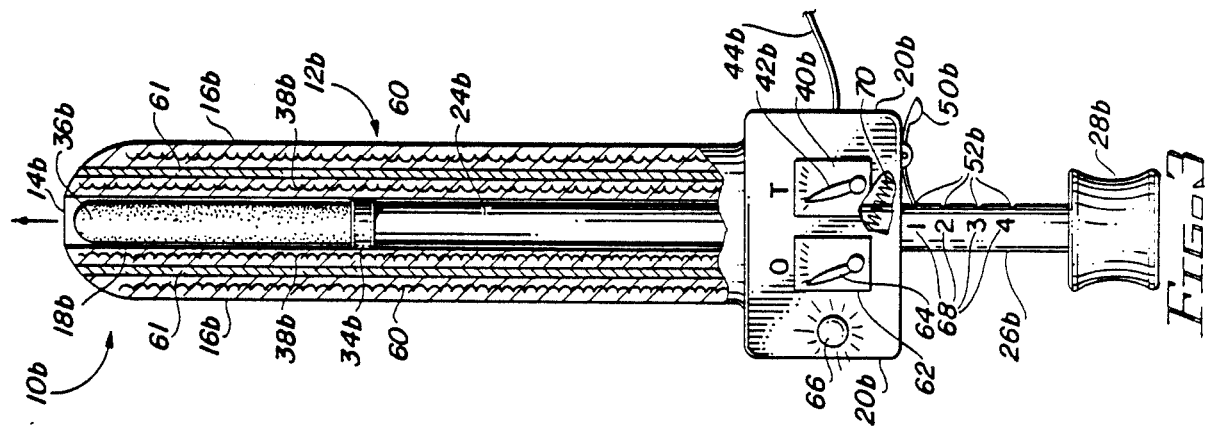
FIG. 3 is a schematic front elevation, partly broken away and partly in section, of a third preferred embodiment of the improved anal medication applicator of the present invention; and, FIG. 4 is a schematic front elevation of the applicator of FIG. 3.

FIGS. 3 and 4

A third preferred embodiment of the improved anal medication applicator of the present invention is schematically depicted in FIGS. 3 and 4. Thus, applicator 10b is shown. Components thereof similar to those of applicators 10 and/or 10a bear the same numerals but are succeeded by the letter "b".

Applicator 10b is substantially identical to applicator 10a, except as follows:
(a) container 12b includes a first set of electrical resistance wiring 38b surrounding cavity 18b containing medication bullet 36b in order to heat bullet 36b through operation of rheostat 40b, lever 42b and wiring 44b; but container 12b also contains a second similar but separate set of electrical resistance wiring 60 disposed adjacent the outer surfaces of sides 16b in order to heat those surfaces to a selected temperature, and separated from wiring 38b by a thermal barrier 61 comprising a foamed plastic sheath or the like. Wiring 60 is connected to rheostat 62 having control lever 64. Rheostat 62 is connected to wiring 44b and is disposed, as is rheostat 38b, in rear portion 20b of container 12b. Portion 20b may also be provided with an electrical light 66 wired to line 44b.
(c) shaft 24b of plunger 26b is marked with numeral gradations 68 at catch holes 52b immediately forward of handle 28b, and a two-armed trigger 50b is rotatably secured to portion 20b and is biased by a spring 70 into a preselected catch hole 52b. Shaft 24b is spring biased forward by spring 32b (FIG. 4). The catch hole 52b selected determines the force applied by head 34b in driving bullet 36b forward out of front end 14b of space 18b, when trigger 50b is fired. Such force controls the depth of penetration of bullet 36b into the anus.
(d) numerical gradations 72 on the sides 16b of container 12b aid in determining the depth of penetration of container into the rectum for controlled delivery of medication thereto.

Applicator 10b has the other advantages of applicators 10 and 10a.

The applicator of the present invention can be made in other forms, sizes and shapes. Thus, the plunger thereof may be electrically actuated or be replaced by a gun-type firing mechanism. In addition, the heating elements of the applicator can be of a type different than that described and electrical power can be provided by batteries instead of house current. Chemically generated heating elements could be employed. Various other modifications, changes, alterations and additions can be made in the improved applicator, its components and parameters. All such changes, modifications, alterations and additions as are within the scope of the appended claims form part of the present invention.

What is claimed is:

1. An improved anal medication-containing applicator, said applicator comprising, in combination:
   a hollow tubular container having an open front end and a generally central space in communication therewith;
   anal medication disposed in said space;
   means connected to said container for heating said medication in said space; and
   means for ejecting said heated anal medication from said space into the anus of a patient;

said heating means comprising a first set of electrical resistance wiring surrounding said space and connected to a rheostat for controlling the temperature of said medication and a second set of electrical resistance wiring adjacent the outer surface of said container, separated from said first set of electrical resistance wiring in said container by a thermal barrier and connected to a second separate rheostat for controlling the surface temperature of said container.

2. The improved applicator of claim 1 wherein said rheostats are connected directly to said container.

3. An improved anal medication-containing applicator, said applicator comprising, in combination:
   a hollow tubular container having an open front end and a generally central space in communication therewith;
   anal medication disposed in said space;
   means connected to said container for heating said medication in said space; and
   means for ejecting said heated anal medication from said space into the anus of a patient and comprising a manually operable plunger abutting the rear of said medication in said space and extending rearwardly out of said container, said plunger being connected to a spring biasing said plunger forward and also connected to catch means connected to said container, for releasably holding said plunger against said biasing, whereby release of said catch means causes sudden spring biasing of said plunger forward to suddenly eject said medication from the front of said container a controlled distance.

4. An improved anal medication-containing applicator, said applicator comprising, in combination:
   a gun-like ejector device comprising a hollow container having an open front end and a gun-like barrel passageway in communication with said front end;
   anal medication disposed in said passageway for movement therein;
   heating means secured to said ejector device for heating said medication prior to ejection; and
   means for ejecting said heated medication from said passageway into the anus of a patient; said heating means comprising a first set of electrical resistance wiring surrounding said space and connected to a rheostat for controlling the temperature of said medication and a second set of electrical resistance wiring adjacent the outer surface of said container, separated from said first set of electrical resistance wiring in said container by a thermal barrier and connected to a second separate rheostat for controlling the surface temperature of said container.

5. The improved applicator of claim 17 wherein said rheostats are connected directly to said container.

6. An improved anal medication-containing applicator, said applicator comprising, in combination:
   a gun-like ejector device comprising a hollow container having an open front end and a gun-like barrel passageway in communication with said front end;
   anal medication disposed in said passageway for movement therein;
   heating means secured to said ejector device for heating said medication prior to ejection; and
   means for ejecting said heated medication from said passageway into the anus of a patient and comprising a plunger abutting the rear of said medication in said passageway and extending rearwardly out of said container, said plunger being connected to a spring biasing said plunger forward and also connected to catch means connected to said container, for releasably holding said plunger against said biasing, whereby release of said catch means causes sudden spring biasing of said plunger forward to suddenly eject said medication from the front of said container a controlled distance.

* * * * *